(12) United States Patent
Kuzelka

(10) Patent No.: US 11,462,140 B2
(45) Date of Patent: Oct. 4, 2022

(54) METHODS AND SYSTEMS FOR DETECTING A MALFUNCTIONING DISPLAY DEVICE

(71) Applicant: GE Precision Healthcare LLC, Wauwatosa, WI (US)

(72) Inventor: Russell J. Kuzelka, Madison, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 107 days.

(21) Appl. No.: 17/039,619

(22) Filed: Sep. 30, 2020

(65) Prior Publication Data

US 2022/0101764 A1 Mar. 31, 2022

(51) Int. Cl.
*G09G 3/00* (2006.01)
*A61M 16/01* (2006.01)
*G06T 1/20* (2006.01)

(52) U.S. Cl.
CPC ............. *G09G 3/006* (2013.01); *A61M 16/01* (2013.01); *G06T 1/20* (2013.01); *A61M 2205/18* (2013.01); *A61M 2205/3306* (2013.01); *A61M 2205/3592* (2013.01); *A61M 2205/52* (2013.01); *A61M 2205/581* (2013.01); *A61M 2205/583* (2013.01);
(Continued)

(58) Field of Classification Search
CPC .............. G09G 3/006; G09G 2330/12; G09G 2380/08; G09G 2370/22; G09G 2360/14; G09G 2360/145; A61M 2205/3306; A61M 2205/3592; A61M 16/01; A61M 2205/18; A61M 2205/52; A61M 2205/583; G06T 1/20
See application file for complete search history.

(56) References Cited

U.S. PATENT DOCUMENTS 6,744,448 B1 * 6/2004 Bernard ................... G06F 3/14
715/764
8,908,902 B2 12/2014 Fifis
2007/0064010 A1 3/2007 Kim
(Continued)

FOREIGN PATENT DOCUMENTS

CN 101369396 B 4/2011
EP 0333136 B1 8/1994

OTHER PUBLICATIONS

International Application No. PCT/US2021/035183 filed Jun. 1, 2021—International Search Report and Written Opinion dated Feb. 4, 2022; 27 pages.

*Primary Examiner* — Phi Hoang

(57) ABSTRACT

Systems and method for detecting malfunctioning display devices are disclosed herein. In one example, a display device for providing information can include a sensor to detect verification data indicating one or more display characteristics of display device output, and a processor to detect a set of configuration images to display using the display device. The processor can also display each configuration image from the set of configuration images and receive verification data from the sensor, wherein the verification data indicates the one or more display characteristics of the display device output. The processor can also determine that the verification data received by the sensor proximate to the display device does not match at least one of the configuration images from the set of configuration images and provide an alert indicating the display device is malfunctioning.

16 Claims, 6 Drawing Sheets

(52) U.S. Cl.
CPC ..... *G09G 2330/12* (2013.01); *G09G 2370/22* (2013.01); *G09G 2380/08* (2013.01)

(56) References Cited

U.S. PATENT DOCUMENTS

| | | |
|---|---|---|
| 2008/0018651 A1 | 1/2008 | Huang |
| 2010/0177114 A1 | 7/2010 | Nakashima |
| 2011/0095899 A1* | 4/2011 | Saito .................. B61L 15/0036 340/691.6 |
| 2013/0128120 A1* | 5/2013 | Chanda .................. H04N 5/63 348/600 |
| 2014/0077094 A1* | 3/2014 | Dinh .................... G01J 1/4204 29/592.1 |
| 2015/0206492 A1 | 7/2015 | Lee |
| 2017/0206864 A1* | 7/2017 | Kp ............................ G06T 1/20 |
| 2018/0061297 A1* | 3/2018 | Schuch ............ H04N 21/41415 |
| 2019/0066307 A1* | 2/2019 | Schneider ............... G06T 13/80 |
| 2020/0233461 A1* | 7/2020 | Kim ...................... G06F 1/1643 |
| 2020/0361383 A1* | 11/2020 | Uken ....................... B60R 1/12 |

* cited by examiner

METHODS AND SYSTEMS FOR DETECTING A MALFUNCTIONING DISPLAY DEVICE

FIELD

Embodiments of the subject matter disclosed herein relate to display devices, and more particularly, to methods and systems for detecting a malfunctioning display device.

BACKGROUND

Computing systems can provide data to users through any number of display devices that are electronically coupled to the computing systems. In some examples, the display devices can malfunction and provide incorrect color values, incorrect illumination levels, or the display devices may not provide any images at all. In critical care settings, incorrect information can result in difficulties when treating patients. For example, a malfunctioning display device that is not providing information to a user may cause a clinician to execute troubleshooting applications and perform additional computing tasks to determine if the computing system is functioning as expected. For critical care computing systems providing anesthesia and performing other critical care functions, a clinician may not have the available resources to analyze a computing system or display device for issues during a surgery, or any other medical service.

SUMMARY

This summary introduces concepts that are described in more detail in the detailed description. It should not be used to identify essential features of the claimed subject matter, nor to limit the scope of the claimed subject matter.

In one aspect, a display device for displaying information can include a sensor to detect verification data indicating one or more display characteristics of display device output and a processor that can detect a set of configuration images to display using the display device. The processor can also display each configuration image from the set of configuration images and receive verification data from the sensor, the verification data indicating the one or more display characteristics of the display device output. In some examples, the processor can determine that the verification data received by the sensor proximate to the display device does not match at least one of the configuration images from the set of configuration images and provide an alert indicating the display device is malfunctioning.

In some examples, the processor can provide the alert using an audio device coupled to the display device. The processor can also provide the alert using a second display device coupled to the display device or using a computing system coupled to the display device. In some examples, the display device can also include a light tube sensor within a bezel of the display device, wherein the light tube sensor provides light from the display device output to a color sensor.

In some aspects, the processor can determine that the verification data received by the sensor proximate to the display device matches the configuration image and provide a confirmation message that the display device is functioning. The processor can also generate the set of configuration images in response to the display device receiving power or in response to a predetermined period of time elapsing or in response to user input. In some examples, the processor can receive the set of configuration images from a remote computing device.

In another aspect, a system for displaying data can include a first processor that can detect a set of configuration images to display using a display device. The first processor can also transmit the set of configuration images to the display device, receive sensor data from the display device, and determine, based on the sensor data, verification data indicating that a color value displayed by the display device does not match a color value of at least one of the configuration images, wherein the color value displayed by the display device is detected from a color sensor coupled to the display device. The first processor can also provide an alert indicating the display device is malfunctioning.

In some examples, the display device can include a second processor that can detect the set of configuration images to be displayed and display each of the configuration images separately. The second processor can also collect the sensor data from the color sensor coupled to the display device as each of the configuration images is displayed and transmit the comparison value to the first processor.

In some aspects, the first processor can detect one or more instructions that cause the display device to display each of the configuration images from the set of configuration images and transmit the one or more instructions to the second processor of the display device. In some examples, the first processor can detect a light intensity value of the display device using a light intensity sensor coupled to the display device, determine that the light intensity value of the display device is below a threshold value, and provide a second alert indicating the light intensity value of the display device is below the threshold value.

In some examples, the first processor can provide the alert using a second display device coupled to the system. The first processor can also provide the alert using an audio device. In some examples, the first processor can detect ambient color data and provide a second alert in response to the ambient color data being below a threshold value. In some aspects, the first processor can be a graphics processing unit.

In some aspects, an anesthesia machine can include a display device, a memory device comprising machine-readable instructions, and a processor to execute the machine-readable instructions, wherein the machine-readable instructions can cause the processor to measure backlight intensity for the display device. In some examples, the machine-readable instructions can cause the processor to determine that the backlight intensity does not match a user programmed intensity and determine that the backlight intensity is below an intensity acceptance threshold. The machine-readable instructions can also cause the processor to transmit the backlight intensity value and a time stamp to a telemetry service.

In some examples, the processor can determine that a maximum allowed drive current is reached, generate a predictive service alert, and transmit the predictive service alert to the telemetry service. The processor can also determine that a maximum allowed drive current is not reached and increase the backlight drive current for the display device.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
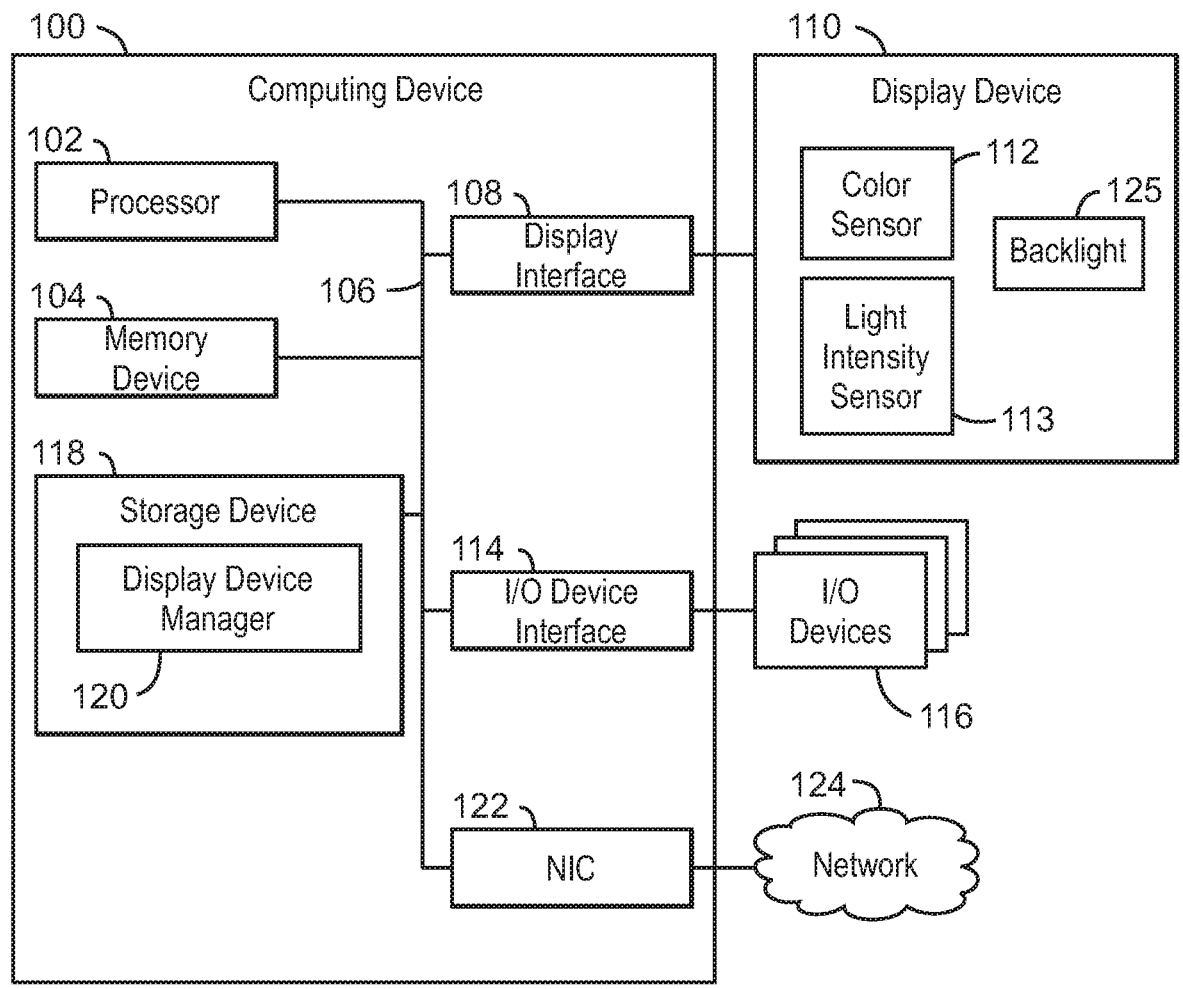
FIG. 1 provides a block diagram of an example computing system that can detect a malfunctioning display device, according to examples herein.

Embodiments of the present disclosure will now be described, by way of example, with reference to the FIGS. 1-7, which relate to various embodiments of a computing system that can detect if a display device is malfunctioning, which can include displaying incorrect color values, displaying images with an incorrect or unexpected illumination level, or the like. In some examples, the techniques herein can also detect if a display device is not displaying any information when electronically coupled to a functioning computing system.

The techniques described herein relate to the real-time verification of a display output image to confirm the display device is functional when used in safety critical user interfaces, among other interfaces. In some examples, user interface display devices (i.e., graphical liquid-crystal displays, such as LCDs, and the like) include an application-specific integrated circuit (ASIC) gate driver, a flex circuit cable, and a backlight driver, among others. The ASIC gate driver can include a system interface receiver that supports various interfaces, such as LVDS, HDMI, MIPI, and eDP, among others. The ASIC gate driver can also include a software control register, an internal or external frame buffer, a gamma reference voltage generator, a timing/control unit, a DC-DC converter booster, a row or gate driver, and a column or data driver, among others. In a typical application, a failure of any one of these elements within the ASIC would prevent transmission of the correct pixel image to the display panel of the display device. Although the ASIC driver may contain a configuration register, the system software may not be able to verify that an image is actually being transmitted to the display panel and is actually visible to a user.

The techniques herein can measure a real-time area of the display's pixels for intensity and color with an electronic color sensor. The area of the display may be predetermined, specified by a user, or otherwise identified. This technique provides immediate feedback to the system that the display is truly functional by monitoring the designated area with a color sensor or combination of a color sensor and light intensity sensor. System display software can be used to command a change to the color of the designated pixel area to verify that the display device is operational and outputting a valid image, which verifies the display driver performance. The system display software can also verify that the intended color is correct compared to the commanded value and enable software diagnostics to control and alter the pixel segment by alternating the color, blanking, or a combination thereof. A color senor and a light intensity sensor can monitor the display device and determine the actual images being displayed. As discussed in greater detail below in relation to FIGS. 1-7, color sensors and light intensity sensors may be embedded in a display device behind a bezel, behind glass of a display device, among other locations, so that the color sensor and the light intensity sensor are hidden from a user's view.

The technical effect of determining when a display device is malfunctioning can enable a computing system to display or otherwise provide data to users with a separate component, communication channel, or a backup display device, among others. The present techniques have a technical advantage of enabling a computing system to determine whether a display device is providing images as expected and to generate an alert if the display device provides or displays unexpected or incorrect colors, an unexpected or incorrect illumination level, or the like. The present techniques can ensure that a user can view or access the data provided from a computing system to a display device without additional troubleshooting actions such as attempting to access the computing device using a remote device. This can prevent the execution of additional applications to determine whether a computing system is functioning in response to a display device connected to the computing system providing a blank screen, or an otherwise altered image to a user.

FIG. 1 is a block diagram of an example of a computing device that can detect a malfunctioning display device. The computing device 100 may be, for example, a hospital monitor, an anesthesia device, a laptop computer, a desktop computer, a tablet computer, or a mobile phone, among others. The computing device 100 may include a processor 102 that is adapted to execute stored instructions, as well as a memory device 104 that stores instructions that are executable by the processor 102. The processor 102 can be a single core processor, a multi-core processor, a computing cluster, or any number of other configurations. The memory device 104 can include random access memory, read only memory, flash memory, or any other suitable memory systems. The instructions that are executed by the processor 102 may be used to implement a method that can detect a malfunctioning display device, as described in greater detail below in relation to FIG. 2.

The processor 102 may also be linked through the system interconnect 106 (e.g., PCI, PCI-Express, NuBus, etc.) to a display interface 108 adapted to connect the computing device 100 to a display device 110. The display device 110 may include a display screen that is a built-in component of the computing device 100. The display device 110 may also include a computer monitor, television, or projector, among others, that is externally connected to the computing device 100. The display device 110 can include light emitting diodes (LEDs), and micro-LEDs, Organic light emitting diode OLED displays, among others.

In some examples, the display device 110 can include a color sensor 112, among other components. The color sensor 112 can be included behind glass of the display device 110, behind a bezel of the display device 110, coupled to the front of the display device 110, or the like. The color sensor 112 can detect any number of colors displayed by the display device 110. The color sensor 112 can provide an output signal indicating one or more detected colors displayed by the display device to the processor 102. In some examples, the color sensor 112 can include logic to determine if the one or more detected colors match an expected or predetermined set of color values. For example, the expected colors can indicate the colors of images transmitted to the display device 110 for display and the output of the color sensor 112 can indicate actual color values provided by the display device 110. The color sensor 112 can perform any number of operations to compare the expected color values to the actual color values or the color sensor 112 can transmit the actual color values to another microprocessor or logic within the display device 112 to determine the comparison of the actual color values and the expected color values. In some examples, the display device 110 can include any additional number of components, such as a light tube (not depicted), light intensity sensor 113, among others, that can enable determining the actual color values and light intensity of the images displayed by the display device 110. Example display devices 110 are described in greater detail below in relation to FIGS. 3, 4, and 5.

The processor 102 may be connected through a system interconnect 106 to an input/output (I/O) device interface 114 adapted to connect the computing device 100 to one or more I/O devices 114. The I/O devices 116 may include, for example, a keyboard and a pointing device, wherein the pointing device may include a touchpad or a touchscreen, among others. The I/O devices 116 may be built-in components of the computing device 100, or may be devices that are externally connected to the computing device 100.

In some embodiments, the processor 102 may also be linked through the system interconnect 106 to a storage device 118 that can include a hard drive, an optical drive, a USB flash drive, an array of drives, or any combinations thereof. In some embodiments, the storage device 118 can include any suitable applications. In some embodiments, the storage device 118 can include a display device manager 120. In some embodiments, the display device manager 120 can generate configuration images to be transmitted to the display device 110. Each configuration image can include one or more colors to be displayed proximate the color sensor 112 of the display device 110. In some examples, each configuration image can include a separate color. The display device manager 120 can also detect, receive, or otherwise obtain output from the color sensor 112 of the display device 100 and determine if the actual color values provided by the display device 110 match the expected one or more color values for each configuration image. In some examples, the display device manager 120 can detect unexpected color values from the color sensor 112 and transmit an alert to another display device, a remote computing device, the display device 110, or any other suitable device (i.e., audible alert upon complete failure of display to produce an image). The alert can indicate that the display device 110 is not providing one or more colors as expected. The alert can also indicate that maintenance is to be scheduled, in some examples, for the display device 110. In some examples, the alert can indicate one or more color values that are incorrect or unexpected, a degradation of color values over time, or the like. If the display device manager 120 determines that the actual color values obtained from a color sensor 112 match the expected color values, the display device manager 120 can provide a confirmation message to the display device 110, a remote computing device, or the like, indicating that the display device 110 is functioning as expected and displaying expected color values. For example, this could be performed as part of the power-on-self-test of the display device and system.

In some examples, the display device manager 120 can also transmit configuration images, configuration settings, and the like, that alter the illumination settings, among other settings, of the display device 110. For example, the display device manager 120 can transmit a configuration setting to the display device 110 that changes the illumination of the display device 110 to a predetermined level or threshold. In some examples, the color sensor 112, a light intensity sensor 113, or any other suitable component within the display device 110 or coupled to the display device 110 can determine the actual light intensity level or output of the display device 110. If the observed or detected light intensity level or output of the display device 110 does not match the expected light intensity level, the display device manager 120 can generate and transmit an alert indicating that the display device 120 is to be serviced, repaired, or otherwise inspected within a period of time.

In some examples, the display device manager 120 can be stored in storage 118, within memory 104 accessible by the processor 102, within the display interface 108, or within the display device 110, among others. For example, the display device manger 120 can be stored within memory of the display interface 108 and a graphics processing unit (not depicted) can execute the instructions of the display device manager 120. In some examples, the display device 110, the display interface 108, the processor 102, and the storage 118 can be connected using any suitable interface, protocol, or the like.

In some examples, a network interface controller (also referred to herein as a NIC) 122 may be adapted to connect the computing device 100 through the system interconnect 106 to a network 124. The network 124 may be a cellular network, a radio network, a wide area network (WAN), a local area network (LAN), or the Internet, among others. The network 124 can enable data, such as alerts, among other data, to be transmitted from the computing device 100 to remote computing devices, remote display devices, and the like. For example, the network 124 may enable remote devices (not depicted) to perform remote services and diagnostics based on sensor data from the display device 110.

In the case of decreasing backlight 125 or color intensity due to aging of the backlight 125 or the display device 110, the computing device 100 can be configured to automatically increase the backlight 125 drive current to restore the intensity to a user defined setting. The amount and duration of drive compensation can be recorded and stored in non-volatile memory 104 such that the computing device 100 can track the health and status of the display device 110 and provide the health and status information to a remote service application via NIC 122 to a network 124 connection, in example. In some examples, the health and status information can include a map of measured light intensity from the display device 100 compared to the applied backlight current. The comparison value can be analyzed, using the computing device 100 or a remote application service, against a predetermined value, such as a value from a manufacturer of the display device 110. If a deviation is detected that exceeds a threshold value, such as a percentage of the original intensity of the display device 110 at a previous drive current, the deviation can be recorded and used to map aging characteristics of the backlight and predict time to failure. Also, if the measured colors of the display device 110 are determined to be shifting, the display device manager 120 can gauge or detect deterioration of the display device 110. For example, the pixels of the display device 110 may appear grayscale due to blocked light output. In some examples, green and red pixels may not illuminate as expected, blue and red pixels may not illuminate as expected, etc. In some examples, the applied backlight 125 drive compensation may continue until the display device 110 assembly is no longer able to compensate, at which time a service alert may be issued by the computing device 100 to inform the user or service personnel that the display device 110 or display backlight 125 will need replacement; eliminating downtime for the user through intelligent and predictive maintenance.

It is to be understood that the block diagram of FIG. 1 is not intended to indicate that the computing device 100 is to include all of the components shown in FIG. 1. Rather, the computing device 100 can include fewer or additional components not illustrated in FIG. 1 (e.g., additional memory components, embedded controllers, additional modules, additional network interfaces, etc.). For example, the display device 110 can include a separate processor that can detect a light intensity value of the display device using a light intensity sensor coupled to the display device, determine that the light intensity value of the display device is below a threshold value, and provide a second alert indicating the light intensity value of the display device is below the threshold value.

Furthermore, any of the functionalities of the display device manager 120 may be partially, or entirely, implemented in hardware and/or in the processor 102. For example, the functionality may be implemented with an application specific integrated circuit, logic implemented in an embedded controller, or in logic implemented in the processor 102, among others. In some embodiments, the functionalities of the display device manager 120 can be implemented with logic, wherein the logic, as referred to herein, can include any suitable hardware (e.g., a processor, among others), software (e.g., an application, among others), firmware, or any suitable combination of hardware, software, and firmware.

Figure 2:
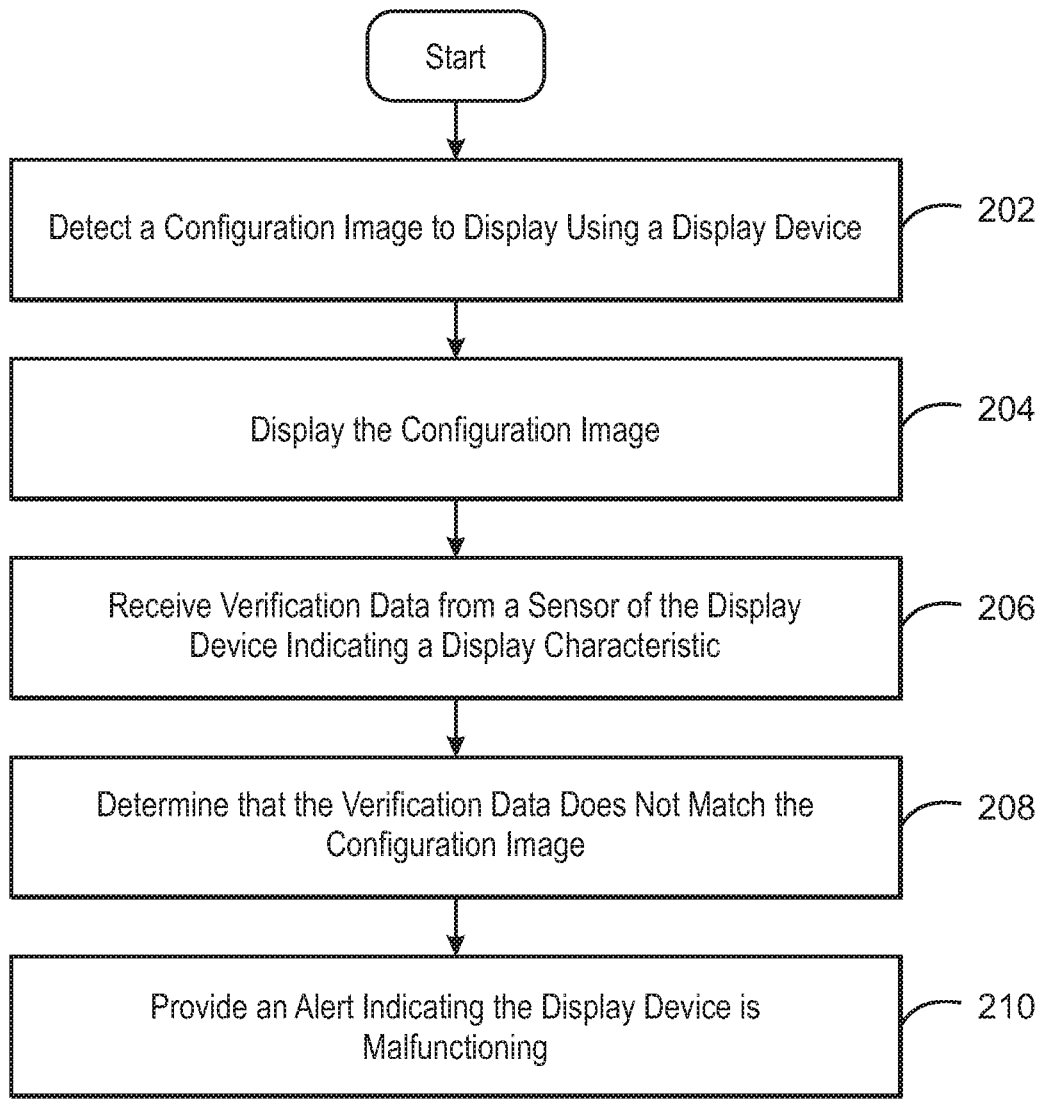
FIG. 2 provides a process flow diagram of an example method for detecting a malfunctioning display device, according to examples herein.

FIG. 2 is a process flow diagram of an example method for detecting a malfunctioning display device. In some examples, the method 200 can be implemented with any suitable computing device, such as the computing device 100 of FIG. 1, or the anesthesia machine 500 of FIG. 5, among others.

At block 202, the method 200 can include detecting a set of configuration images to display using the display device. In some examples, each configuration image can include a single color value. For example, each configuration image can be a different color, such as red, green, blue, and the like. In some examples, each configuration image can include a single color value adjacent to a portion of the display device. For example, an area or region of each configuration image adjacent to a color sensor or a light tube, among other sensors, can be a single value such as red, green, blue, or the like.

In some examples, the configuration images can enable a color sensor or a light tube, among others, to determine if an unexpected color is projected by the display device. A display device can include multiple colors sensors or light tubes in some examples. A configuration image can include one or more colors to enable each color senor to simultaneously determine if a display device is providing an expected color value within a predetermined area of the display device. For example, a first area of the configuration image may display a first color adjacent to a first color sensor or light tube. Additionally, a second area of the configuration image may display a second color adjacent to a second color sensor or light tube.

In some examples, the configuration images can also be displayed with different display settings such as a different light intensity, a different contrast, a different color ratio, or the like. The display settings for the configuration images can be detected with the color sensor or the light tube, among other sensors, to determine whether a display device is functioning as expected.

Still at block 202, in some examples, the method 200 can include generating the set of configuration images in response to the display device receiving power. For example, the configuration images can be created or generated each time a display device is turned on or each time a computing system electronically coupled to the display device receives power and attempts to display information using the display device. In some examples, the configuration images can be created or generated in response to a predetermined period of time elapsing. For example, the configuration images can be created or generated every suitable number of seconds, minutes, hours, weeks, months, or the like. In some examples, the method 200 can include generating or creating the configuration images at a predetermined static period of time or the configuration images can be created or generated based on dynamic time periods. For example, the method 200 can create or generate configuration images to be displayed more frequently in response to detecting a shift in output color values or an output light intensity of the display device.

In some examples, the method 200 can include generating or creating the configuration images in response to user input, such as a request to validate that a display device is functioning as expected. In some examples, the method 200 can include detecting the set of configuration images from a remote computing system, or any other suitable source. The method 200 can also include storing copies of a set of configuration images to use to obtain display device output. For example, the method 200 can generate or create a set of configuration images, store the set of configuration images in memory within the display device or within a computing system coupled to the display device, and provide the stored set of configuration images to the display device each time the display device is to be validated.

At block 204, the method 200 can include displaying each configuration image from the set of configuration images. For example, the configuration images can be stored in a frame buffer of the display device and loaded from the frame buffer to display or provide each configuration image using the display device. In some examples, each configuration image can be displayed for a predetermined period of time, a dynamic period of time, or the like. For example, a red image, a green image, and a blue image can each be displayed for a period of time, such as 5 milliseconds, 100 milliseconds, or 1 second, among others. In some examples, the configuration images can be displayed each time the display device receives power, each time the display device is initiated, or during a predetermined period of time to periodically evaluate the display device, among others. For example, the configuration images can be displayed each hour, each day, each week, or the like.

In some examples, the color sensor or the light tube can detect the color of each configuration image, or an intensity of light for each configuration image, among other characteristics or display settings. As discussed above, each configuration image can include one or more color values included in any suitable arrangement, pattern, or sequence. In some examples, the display settings for providing the configuration images with the display device can also be modified to detect a degradation of components of the display device. For example, a decrease in intensity of a configuration image, an unexpected color value being displayed, or the like, can indicate a malfunctioning display device.

In some examples, the method 200 can include detecting, with a computing system coupled to the display device, one or more instructions that cause the display device to display each of the configuration images from the set of configuration images. The method 200 can also include transmitting the one or more instructions to a processor of the display device from a processor of the computing system coupled to the display device.

At block 206, the method 200 can include receiving verification data from the sensor, wherein the verification data indicates any number of display characteristics of the display device output. The display characteristics, as referred to herein, can include a color value representing an area of a display device proximate a sensor, an illumination level or intensity of the display device, or an ambient color value representing an area of a display proximate a sensor, among others.

At block 208, the method 200 can include determining that verification data received by the color sensor proximate to the display device does not match the configuration image. For example, the verification data can indicate an actual color value, intensity value, or the like, detected from the display panel in response to displaying each configuration image. The verification data can be collected, detected, or otherwise obtained from a color sensor proximate to the display device, a light tube proximate to the display device, or any other suitable sensor or combination of sensors or components. The verification data can include any suitable value, such as an ascii value, among others, that indicates a color detected by a color sensor. In some examples, the verification data can include at least one output value from each color sensor, light tube, light intensity sensor, or a combination thereof. The output value from a light intensity sensor can include any numeric or alphanumeric value that indicates a brightness of a portion of the pixels of a display device. In some examples, the color sensor or the light tube can be mounted within a bezel of the display device, embedded in the glass of the display device, or coupled to the display device and placed within a predetermined distance from the display device. If the verification data does not match the configuration image, the display device is malfunctioning and is to be repaired, reconfigured, or otherwise serviced. If the verification data matches the configuration image, the display device is functioning.

At block 210, the method 200 can include providing an alert indicating the display device is malfunctioning. In some examples, the alert can be provided to a user using a backup or second display device, using an audio device, or using the display device. The alert can indicate that the display device is not displaying one or more colors as expected, or that the display device is not displaying images with an expected light intensity, among others. The computing system providing information to the display device can continue to operate or function as expected. For example, a ventilator or anesthesia machine coupled to the display device can continue to operate without the display device as the alert is provided to a backup display device or a remote computing device.

In some examples, the alert can also indicate that the ambient color of a display device is not as expected. For example, the color sensor may resolve any number of colors up to 16 bits per pixel color or up to 65,536 individual colors, or any other suitable number of colors. In some examples, the color sensor, or any other sensor, can also measure the light color temperature and ambient light for the backlight of the display device. In some examples, the color sensor can detect ambient light that indicates a degrading backlight of the display.

In some examples, a confirmation message verifying that the display device is functioning as expected can be transmitted to a user via the display device, an audio device coupled to the display device, using a second display device, or the like. The computing device coupled to the display device can continue to operate or function as expected whether the display device is functional or non-functional.

The process flow diagram of method 200 of FIG. 2 is not intended to indicate that all of the operations of blocks 202-210 of the method 200 are to be included in every example. Additionally, the process flow diagram of method 200 of FIG. 2 describes a possible order of executing operations. However, it is to be understood that the operations of the method 200 can be implemented in various orders or sequences. In addition, in some examples, the method 200 can also include fewer or additional operations. For example, the method 200 can include determining if a display device fails to display a number of consecutive or non-consecutive configuration images that exceeds a threshold value. If the display device fails to display a number of configuration images that exceeds the threshold value, the method 200 can include automatically switching the display data path to an alternate or backup display device. For example, if the display device fails to display the expected colors with two configuration images and the threshold is configured as a value of two, the display device may be powered off and display data previously transmitted to the display device can be transmitted to an alternate display device.

In some examples, the method 200 can be performed using a display device that includes at least a color sensor or light tube and logic, such as a processor, among others, to detect and compare the verification data to the configuration images. In some examples, the method 200 can include detecting a set of configuration images to display using a display device. The display device can detect, receive, or otherwise obtain the set of configuration images from an external device or generate the configuration images within the display device. In some examples, a computing device electronically coupled to the display device can detect, receive, or otherwise obtain the set of configuration images and transmit the set of configuration images to the display device. The display device may detect, collect, or obtain sensor data as each configuration image is displayed and transmit the sensor data to the computing device to determine if the sensor data matches the expected color values or light intensity of each configuration image. In some examples, a color sensor of a display device may have read and write functionality that enables the color sensor to detect or read an expected color value for each configuration image, collect sensor data as each configuration image is displayed, perform a comparison of the actual collected color value to the expected color value, and write the output of the comparison to any suitable source, such as memory with the display device, a remote computing device, a register, or the like. In some examples, the computing device coupled to the display device can receive sensor data from a color sensor, light tube sensor, or light intensity sensor, among others. The computing device can also determine, based on the sensor data, that verification data does not match an expected color value or intensity of a configuration image and the computing device can generate and provide an alert through an audio device, a separate display device, or the like. The alert can be provided as an interrupt that has a higher priority than other instructions, which causes a computing system to provide the alert in real-time to any suitable remote device, display device, light or audio component, among others.

Figure 3:
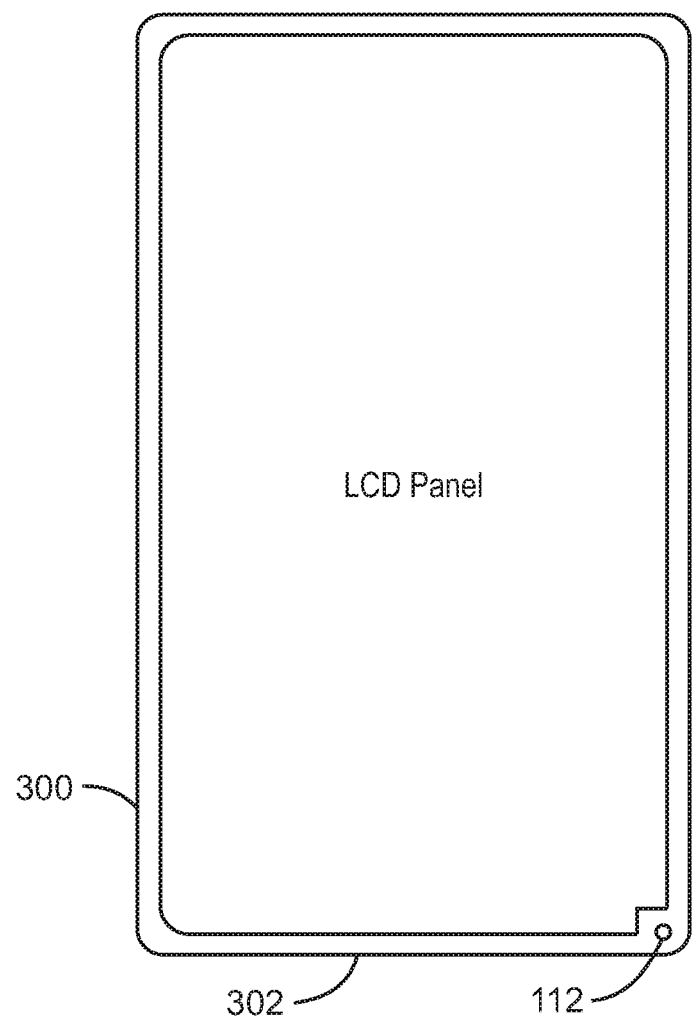
FIG. 3 provides a schematic diagram of an example display device with a color sensor for detecting a malfunctioning display device, according to examples herein.

FIG. 3 provides a schematic diagram of an example display device with a color sensor for detecting a malfunctioning display device, according to examples herein. The color sensor 112 can filter colors based on red, green, blue, clear, or any suitable color. In some examples, the color sensor 112 can be included behind glass of a display device 300, incorporate into a substrate of the display device 300, or embedded in any suitable location of the display device 300 that receives light projected or otherwise provided by the display device 300. In some examples, a color sensor 112 can be included along any suitable edge of the display panel 300 behind a bezel 302. For example, the color sensor 112 can be included behind a bezel 302 along an edge of the display device 300 and the configuration images can be predetermined with one or more values to be detected by the color sensor 112. In some examples, the color sensor 112 can be included in the bezel 302 of a display device 300 behind a hole or any suitable diameter or shape, which enables light provided by the display device 300 to be detected by the color sensor 112.

In some examples, any number of color sensors 112 can be coupled to a display device 300 or embedded in the display device 300. The color sensors 112 can each detect one or more color values and the output of the color sensors 112 can be analyzed by logic of the display device 300 or a connected computing system. The combination of the color sensor 112 output values can indicate particular regions of a display device 300 that are providing an unexpected or incorrect color value, an incorrect ambient color, or the like. In some examples, a light intensity sensor (not depicted) can also be included proximate to the color sensors 112, or along any suitable portion of a display device 300. The light intensity sensor (not depicted) can detect the illumination level or light intensity level of the display device 300 and provide an output value indicating whether the display device 300 is providing an incorrect illumination level or threshold.

Figure 4:
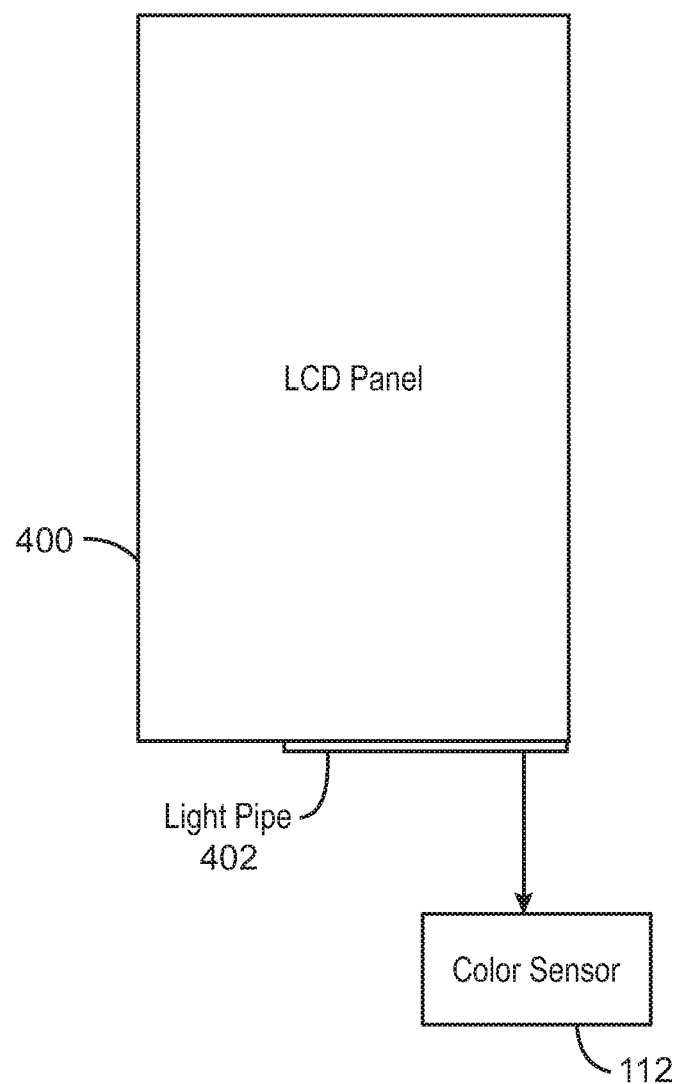
FIG. 4 provides a schematic diagram of an example display device with a light tube for detecting a malfunctioning display device, according to examples herein.

FIG. 4 provides a schematic diagram of an example display device with a light tube for detecting a malfunctioning display device, according to examples herein. In some examples, the light tube 402 can provide light collected from the display panel 400 to a color sensor 112, or any other suitable component. In some examples, the color sensor 112 can analyze the collected light to determine a color value of the image being displayed by the display device 400, an intensity of the image being displayed by the display device 400, an ambient color of the image being displayed by the display device 400, and the like. In some examples, the light tube 402 can be located along any portion of a display device 400, such as a left area of the display device 400, a right area of the display device 400, a top of the display device 400, or a bottom of the display device 400. In some examples, the light tube 402 can be located along an entire side of a display device 402 or along a portion of a side of the display device 400.

In some examples, the light tube 402 can include a color sensor 112 that determines a color value provided by a display device 400. One or more light tubes 402 can be included in a display device 400 to determine the color values provided by any number of regions or areas of the display device 400. For example, each edge of a display device 400 may include a different light tube 402 and each light tube 402 can detect a color displayed by a separate area or region of the display device 400.

Figure 5:
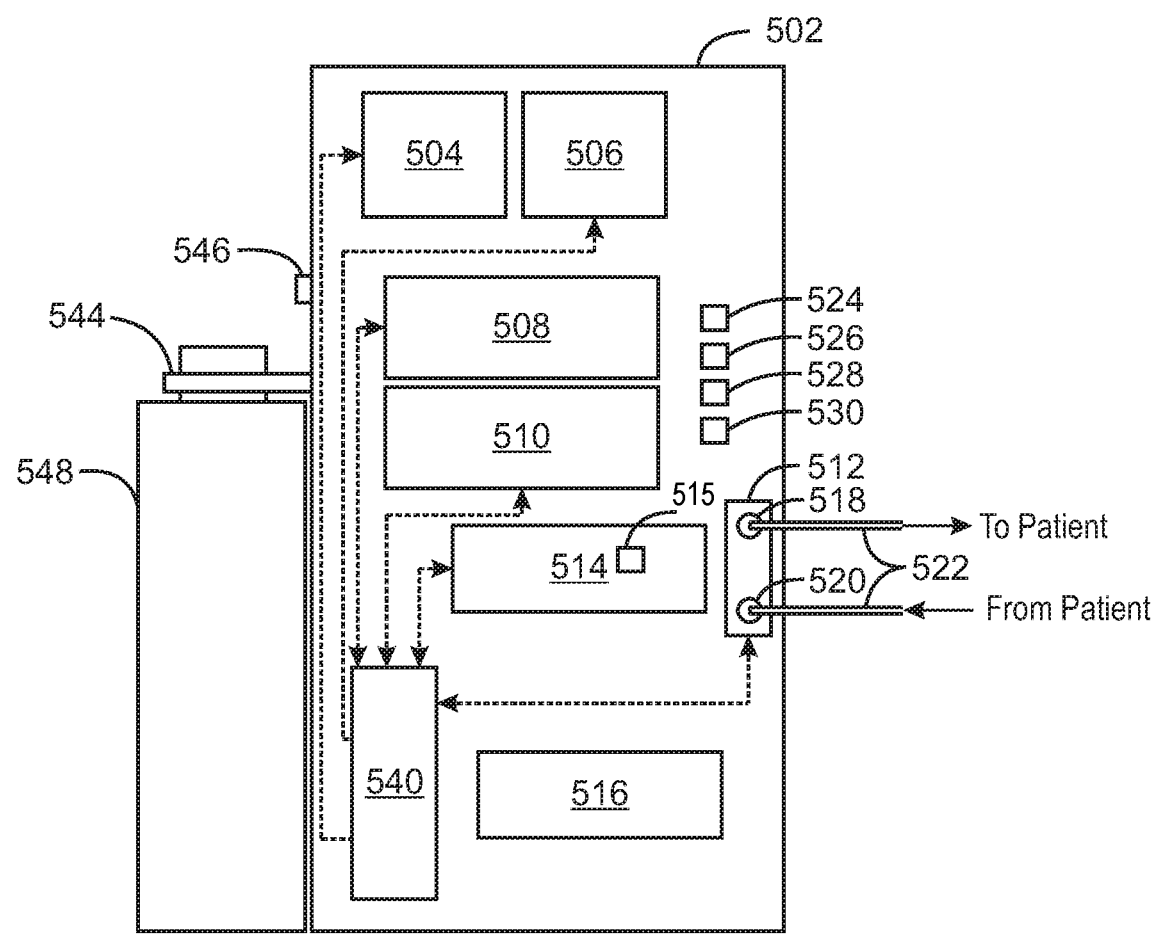
FIG. 5 schematically shows an example block diagram of an anesthesia machine that can detect a malfunctioning display device, according to an example herein.

FIG. 5 schematically shows an example anesthesia 500. Anesthesia machine 100 includes a frame (or housing) 502. In some embodiments, frame 502 may be supported by casters, where the movement of the casters may be controlled (e.g., stopped) by one or more locks. In some examples, the frame 502 may be formed of a plastic material (e.g., polypropylene). In other examples, the frame 502 may be formed of a different type of material (e.g., metal, such as steel).

Anesthesia machine 500 also includes an anesthesia display device 504, a patient monitoring display device 506, a respiratory gas module 508, one or more patient monitoring modules, such as a patient monitoring module 510, a ventilator 512 (explained in more detail below), an anesthetic vaporizer 514, and an anesthetic agent storage bay 516. Anesthesia machine 500 may further include a main power indicator 524, a system activation switch 526 (which, in one example, permits gas flow when activated), an oxygen flush button 528, and an oxygen control 530. Anesthetic vaporizer 514 may vaporize the anesthetic agent and combine the vaporized anesthetic agent with one or more medical grade gases (e.g., oxygen, air, nitrous oxide, or combinations thereof), which may then be delivered to a patient.

Anesthesia machine 500 may additionally include an integrated suction, an auxiliary oxygen flow control, and various other components for providing and/or controlling a flow of the one or more medical grade gases to the patient. For example, anesthesia machine 500 includes one or more pipeline connections 546 to facilitate coupling of the anesthesia machine to pipeline gas sources. Additionally, anesthesia machine 500 includes a cylinder yoke 544, via which one or more gas-holding cylinders 548 may be coupled to the anesthesia machine. Thus, through the pipeline connection and/or cylinder connections, gas may be provided to the anesthesia machine, where the gas may include (but is not limited to) medical air, oxygen, nitrogen, and nitrous oxide. The gas that enters the anesthesia machine may mix with the vaporized anesthetic agent at the anesthetic vaporizer 514, as described above, before being supplied to a patient via the ventilator 512. The anesthesia machine may also include a serial port, a collection bottle connection, a cylinder wrench storage area, and an anesthesia gas scavenging system.

The ventilator 512 may include an expiratory check valve at an expiratory port 520, an expiratory flow sensor at the expiratory port 520, an inspiratory check valve at an inspiratory port 518, an inspiratory flow sensor at the inspiratory port 518, an absorber canister, a manual bag port, a ventilator release, an adjustable pressure-limiting valve, a bag/vent switch, and a bellows assembly. When a patient breathing circuit is coupled to the ventilator 512, breathing gases (e.g., air, oxygen, and/or nitrous oxide mixed with vaporized anesthetic agent) exit the anesthesia machine from the inspiratory port 518 and travel to the patient. Expiratory gases from the patient re-enter the anesthesia machine via the expiratory port 520, where carbon dioxide may be removed from the expiratory gases via the absorber canister.

During operation of the anesthetic vaporizer 514, an operator (e.g., an anesthesiologist) may adjust an amount of vaporized anesthetic agent that is supplied to the patient by adjusting a flow rate of gases from the gas source(s) (e.g., the pipeline gas supply) to the vaporizer. The flow rate of the gases from the gas source to the vaporizer may be adjusted by the operator via adjustment of one or more flow adjustment devices. For example, the flow adjustment devices may include analog and/or digital adjustment dials and/or other user input devices configured to actuate one or more flow control valves of anesthesia machine 500. In some embodiments, a first flow control valve may be positioned between the gas source(s) and the anesthetic vaporizer 514 and may be actuatable via the flow adjustment devices to a fully opened position, a fully closed position, and a plurality of positions between the fully opened position and the fully closed position.

Anesthesia machine 500 may additionally include one or more valves configured to bypass gases from the gas source(s) around the anesthetic vaporizer 514. The valves may enable a first portion of gases to flow directly from the gas source to the inspiratory port 518 and a second portion of gases to flow from the gas source through the anesthetic vaporizer 514 to mix with the vaporized anesthetic agents prior to flowing to the inspiratory port 518. By adjusting a ratio of the first portion of gases relative to the second portion of gases, the operator may control a concentration of vaporized anesthetic agent administered to the patient via the inspiratory port 518.

Further, the adjustments described above may be facilitated at least in part based on output from the respiratory gas module 508. The respiratory gas module 508 may be configured to measure various parameters of the gases exiting the vaporizer and/or being provided to the patient. For example, the respiratory gas module 508 may measure the concentrations of carbon dioxide, nitrous oxide, and the anesthetic agent provided to the patient. Further, the respiratory gas module 508 may measure respiration rate, minimum alveolar concentration, patient oxygen, and/or other parameters. The output from the respiratory gas module 508 may be displayed via a graphical user interface on a display device (e.g., the anesthesia display device 504 and/or the patient monitoring display device 506) and/or used by a controller to provide closed-loop feedback control of the amount of anesthesia provided to the patient.

The ventilator 512 may optionally be coupled to a breathing circuit (not shown) including a plurality of tubes (e.g., gas passages) 522. The breathing circuit may be coupled between an airway of a patient (e.g., via a breathing mask positioned to enclose the mouth and/or nose of the patient or a tracheal intubation tube) and the inspiratory port 518. Gases (e.g., the one or more medical gases, or a mixture of the one or more medical gases and vaporized anesthetic agent from the anesthetic vaporizer 514) may flow from the inspiratory port 518, through the breathing circuit, and into the airway of the patient, where the gases are absorbed by the lungs of the patient. By adjusting the concentration of vaporized anesthetic agent in the gases as described above, the operator may adjust a degree to which the patient is anesthetized.

During conditions in which the breathing circuit is coupled to the airway, the anesthetic agent and/or fresh gas (without the anesthetic agent) may flow into the airway of the patent (e.g., through inhalation) via the inspiratory port 518 and the inspiratory check valve. As an example, the inspiratory check valve may open automatically (e.g., without input or adjustment by the operator) in response to inhalation by the patient and may close automatically in response to exhalation by the patient. Similarly, the expiratory check valve may open automatically in response to exhalation by the patient and may close automatically in response to inhalation by the patient.

In some embodiments, the operator may additionally or alternatively control one or more operating parameters of the anesthesia machine 500 via an electronic controller 540 of the anesthesia machine 500. Controller 540 includes a processor operatively connected to a memory. The memory may be a non-transitory computer-readable medium and may be configured to store computer executable code (e.g., instructions) to be processed by the processor in order to execute one or more routines, such as those described herein. The memory may also be configured to store data received by the processor. Controller 540 may be communicatively coupled (e.g., via wired or wireless connections) to one or more external or remote computing devices, such as a hospital computing system, and may be configured to send and receive various information, such as electronic medical record information, procedure information, and so forth. Controller 540 may also be electronically coupled to various other components of the anesthesia machine 500, such as the anesthetic vaporizer 514, the ventilator 512, the respiratory gas module 508, the anesthesia monitoring display device 504, and the patient monitoring display device 506.

In some examples, the controller 540 can execute instructions that implement the functionality of the display device manager 120. For example, the controller 540 can transmit configuration images to the anesthesia monitoring display device 504, the patient monitoring display device 506, or a combination thereof The anesthesia monitoring display device 504 and the patient monitoring display device 506 may each include any number of color sensors, light tubes, light intensity sensors, or a combination thereof. The anesthesia monitoring display device 504 and the patient monitoring display device 506 can perform any number of the operations of method 200 described above in relation to FIG. 2 in order to determine if the anesthesia monitoring display device 504 and the patient monitoring display device 506 are functioning properly. In some examples, an alert indicating that either the anesthesia monitoring display device 504 or the patient monitoring display device 506 is malfunctioning can be provided with an audio component of the anesthesia machine 500, an audio component electronically coupled to the anesthesia machine 500, or any suitable number of lights within the anesthesia machine 500 or electronically coupled to the anesthesia machine 500. The alert can also be provided with either the anesthesia monitoring display device 504 or the patient monitoring display device 506 or the anesthetic vaporizer display device 515. For example, if the anesthesia monitoring display device 504 is not functioning as expected, the alert can be displayed with the patient monitoring display device 506 and/or the anesthetic vaporizer display device 515. Also, if the patient monitoring display device 506 is not functioning, the alert can be displayed with the anesthesia monitoring display device 504 and/or the anesthetic vaporizer display device 515.

In some examples, the anesthetic vaporizer 514 may also have an anesthetic vaporizer display device 515. If the anesthetic vaporizer display device 515 fails, information about the anesthetic vaporizer display device 515 may be provided on the anesthesia display device 504 as a recourse for safety during a surgical case, and vice-versa. If the anesthesia display device 504 fails to output an image, the system may recognize the fault and transmit a subset of critical waveforms or text field data to the anesthetic vaporizer display device 515.

In some examples, the controller receives signals from the various sensors of the anesthesia machine 500 and employs the various actuators of the anesthesia machine 500 to adjust operation of the anesthesia machine 500 based on the received signals and instructions stored on the memory of the controller. For example, the flow of gases to the inspiratory port 518 may be controlled via an input device (e.g., keyboard, touchscreen, etc.) coupled to the electronic controller of the anesthesia machine 500. The controller 540 may display operating parameters of the anesthesia machine 500 via the anesthesia display device 504 and/or the patient monitoring display device 506. The controller may receive signals (e.g., electrical signals) via the input device and may adjust operating parameters of the anesthesia machine 500 in response (e.g., responsive) to the received signals.

As one example, the operator may input a desired concentration of the anesthetic agent to be delivered to the patient. A corresponding valve position of one or more valves of the anesthesia machine (e.g., a position of one or more bypass valves, as described above) may be empirically determined and stored in a predetermined lookup table or function in a memory of the controller. For example, the controller may receive the desired concentration of the anesthetic agent via the input device and may determine an amount of opening of the one or more valves corresponding to the desired concentration of the anesthetic agent based on the lookup table, with the input being the concentration of the anesthetic agent and the output being the valve position of the one or more valves. The controller may transmit an electrical signal to an actuator of the one or more valves in order to adjust each of the one or more valves to the corresponding output valve position. In some examples, the controller may compare the desired flow rate of gases to a measured flow rate of gases, such as measured by the inspiratory flow sensor, for example. In some examples, if the information which was being displayed on the failing or failed display device is transferred to an alternate display, the alternate display may be configured to detect commands for a system in a recourse and recovery mode. For example, if the patient monitoring display device 506 is not functioning, the anesthesia monitoring display device 504 or the anesthetic vaporizer display device 515 can detect commands for the system in a recovery mode.

Controller 540 is shown in FIG. 5 for illustrative purposes, and it is to be understood that controller 540 may be located in various locations within, around, and/or remote from anesthesia machine 500. As an example, controller 540 may include multiple devices/modules that may be distributed throughout anesthesia machine 500. As such, controller 540 may include a plurality of controllers at various locations within anesthesia machine 500. As another example, additionally or alternatively, controller 540 may include one or more devices/modules that are external to anesthesia machine 500, located proximate to (e.g., in a same room) or remote from (e.g., a remote server) anesthesia machine 500. In each example, the multiple devices/modules may be communicatively coupled through wired and/or wireless connections.

Anesthetic vaporizers, such as anesthetic vaporizer 514 shown in FIG. 5, may employ various methods to vaporize a liquid anesthetic agent. For example, the anesthetic vaporizer may use a flow-over method (in which a carrier gas flows over a top surface of a volatile liquid anesthetic agent), a bubble-through method (in which the carrier gas is bubbled up through the liquid anesthetic agent), or a gas/vapor blender (in which heat is used to vaporize the liquid anesthetic agent, and the vapors are injected into a fresh gas flow). Regardless of the vaporization method, the anesthetic vaporizer 514 may include a sump for storing the liquid anesthetic agent before it is delivered to a vaporizing chamber. Further, in each example, the liquid anesthetic agent may leak from the sump to other components of the vaporizer or to atmosphere, such as when various seals become worn or otherwise degraded.

Figure 6:
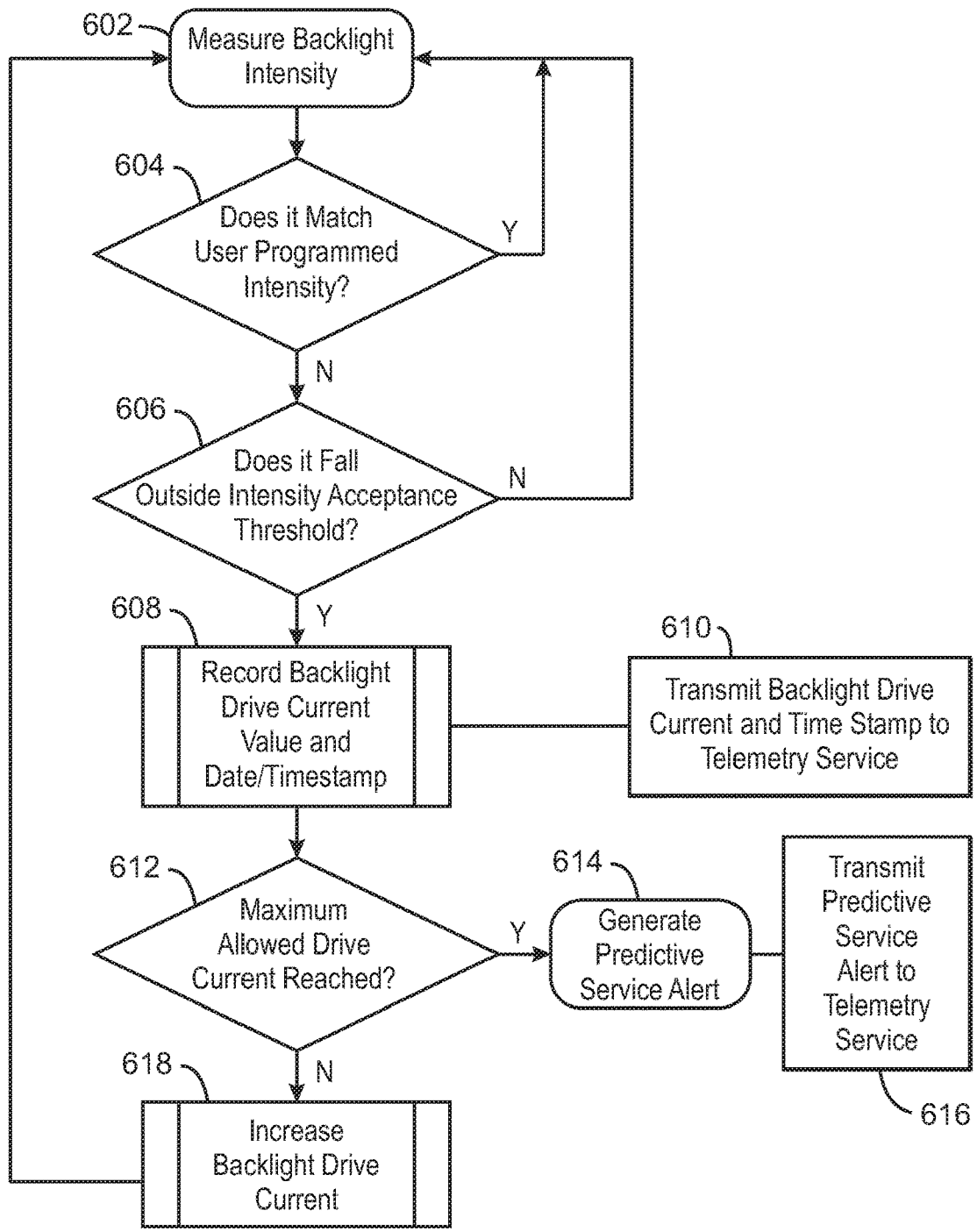
FIG. 6 is a process flow diagram of an example method for generating a predictive service alert for a display device, according to examples herein.

FIG. 6 is a process flow diagram of an example method for generating a predictive service alert for a display device, according to examples herein. The method 600 can be implemented with any suitable computing device, display device, or a combination thereof, such as the computing system 100 and display device 110 of FIG. 1 or the anesthesia machine 500 of FIG. 5, among others.

At block 602, the method 600 can include measuring backlight intensity of a display device. In some examples, any suitable sensor, such as a color sensor, light intensity sensor, or the like, can be coupled to a display device. The sensor can measure the backlight intensity of the display device as configuration images are displayed.

At block 604, the method 600 can include determining whether the measured backlight intensity matches a user programmed intensity. For example, the user programmed intensity can indicate a brightness of a display device, or any other suitable configurable setting. The user programmed intensity can modify the brightness of the configuration images displayed by the display device. If the backlight intensity matches the user programmed intensity, the method 600 can return to block 602. If the backlight intensity does not match the user programmed intensity, the method 600 can continue at block 606.

At block 606, the method 600 can include determining if the measured backlight intensity is below or above an intensity acceptance threshold. For example, the intensity acceptance threshold can indicate a minimum brightness or intensity of light for one or more of the configuration images. If the measured backlight intensity is above the intensity acceptance threshold, the method 600 can return to block 602. If the measured backlight intensity is below the intensity acceptance threshold, the method 600 can continue at block 608.

At block 608, the method 600 can include recording a backlight drive current for the display device along with a timestamp indicating a time, date, or a combination thereof. In some examples, the method 600 can include transmitting, at block 610, the backlight drive current and timestamp to a telemetry service, such as a local telemetry service or a remote telemetry service, or any other suitable device or service. The remote telemetry service, or any suitable data repository within a computing device or electronically coupled to the display device, can store the backlight drive current and timestamp. In some examples, the telemetry service can include any suitable service that is stored and executed by one or more remote devices. The telemetry service can monitor the backlight drive current for any number of display devices.

In some examples, at block 612, the method 600 can include determining if a maximum allowed drive current has been reached. The maximum allowed drive current, as referred to herein, can include any predetermined or configurable value that represents a drive current for a backlight of a display device that cannot be exceeded without damaging the display device. If the measured backlight drive current has been reached, the method 600 can include generating, at block 614, a predictive service alert that indicates a display device is no longer functioning within a predetermined light intensity range. The predictive service alert can be transmitted, at block 616, to the telemetry service. In some examples, the telemetry service can initiate a repair request so that the display device associated with the predictive service alert is either repaired or replaced prior to the display device failing.

At block 612, if the maximum backlight drive current has not been reached, the method 600 can include increasing, at block 618, the backlight drive current and returning to block 602.

The process flow diagram of method 600 of FIG. 6 is not intended to indicate that all of the operations of blocks 602-618 of the method 600 are to be included in every example. Additionally, the process flow diagram of method 600 of FIG. 6 describes a possible order of executing operations. However, it is to be understood that the operations of the method 600 can be implemented in various orders or sequences. In addition, in some examples, the method 600 can also include fewer or additional operations.

Figure 7:
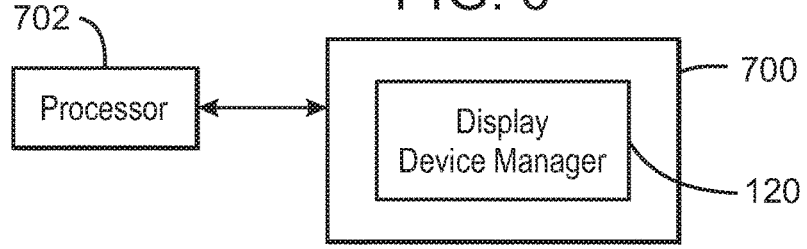
FIG. 7 provides a block diagram of an example non-transitory machine-readable medium for detecting a malfunctioning display device, according to examples herein.

FIG. 7 is an example of a non-transitory machine-readable medium for detecting a malfunctioning display device, in accordance with examples described herein. The non-transitory, machine-readable medium 700 can cause a processor 702 to implement the functionalities of methods 200 and 600. For example, a processor of a computing device (such as processor(s) 102 of computing device 100 of FIG. 1), or any other suitable device, can access the non-transitory, machine-readable media 700.

In some examples, the non-transitory, machine-readable medium 700 can include instructions to execute a display device manager 120. For example, the non-transitory, machine-readable medium 700 can include instructions for the display device manager 120 that cause the processor 702 to transmit configuration images to a display device, receive verification data from the display device, and determine if the display device is providing unexpected or incorrect color values, illumination levels, or the like. The display device manager 120 can also generate an alert and transmit the alert to any suitable computing device or display device in response to detecting a mismatch between the actual color values or illumination values of the display device and the expected color values or illumination values. In some examples, the non-transitory, machine-readable medium 700 can include instructions to implement any combination of the techniques of the methods 200 and 600 described above.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A display device for displaying information comprising:
   a first sensor to detect verification data indicating one or more display characteristics of display device output, wherein a light tube within a bezel of the display device provides light from the display device to the first sensor; and
   a processor to:
      detect a set of configuration images to display using the display device;
      display each configuration image from the set of configuration images;
      receive verification data from the first sensor, the verification data indicating the one or more display characteristics of the display device output;
      determine that the verification data received by the first sensor proximate to the display device does not match at least one of the configuration images from the set of configuration images; and
      provide an alert indicating the display device is malfunctioning.

2. The display device of claim 1, wherein the processor is to provide the alert using an audio device coupled to the display device.

3. The display device of claim 1, wherein the processor is to provide the alert using a second display device coupled to the display device or using a computing system coupled to the display device.

4. The display device of claim 1, wherein the processor is to determine that the verification data received by the first sensor proximate to the display device matches the configuration image and provide a confirmation message that the display device is functioning.

5. The display device of claim 1, wherein the set of configuration images comprise one or more images that each include a different color to be displayed proximate to the first sensor, and wherein the first sensor is a color sensor, a light intensity sensor, or a combination thereof.

6. The display device of claim 1, wherein the processor is to generate the set of configuration images in response to the display device receiving power or in response to a predetermined period of time elapsing or in response to user input.

7. The display device of claim 1, wherein the processor is to receive the set of configuration images from a remote computing device.

8. A system for displaying data comprising:
   a first processor to:
      detect a set of configuration images to display using a display device;
      transmit the set of configuration images to the display device;

receive sensor data from the display device;

determine, based on the sensor data, verification data indicating that a color value displayed by the display device does not match a color value of at least one of the configuration images, wherein the color value displayed by the display device is detected from a color sensor coupled to the display device, and wherein a light tube within a bezel of the display device provides light from the display device to the color sensor; and provide an alert indicating the display device is malfunctioning.

9. The system of claim 8, wherein the display device comprises a second processor to:

detect the set of configuration images to be displayed;

display each of the configuration images separately;

collect the sensor data from the color sensor coupled to the display device as each of the configuration images is displayed; and transmit the color value to the first processor.

10. The system of claim 9, wherein the first processor is to:

detect one or more instructions that cause the display device to display each of the configuration images from the set of configuration images; and transmit the one or more instructions to the second processor of the display device.

11. The system of claim 8, wherein the set of configuration images is stored in a frame buffer.

12. The system of claim 8, wherein the first processor is to:

detect a light intensity value of the display device using a light intensity sensor coupled to the display device;

determine that the light intensity value of the display device is below a threshold value; and provide a second alert indicating the light intensity value of the display device is below the threshold value.

13. The system of claim 8, wherein the first processor is to provide the alert using a second display device coupled to the system.

14. The system of claim 8, wherein the first processor is to provide the alert using an audio device.

15. The system of claim 8, wherein the first processor is to:

detect ambient color data; and provide a second alert in response to the ambient color data being below a threshold value.

16. The system of claim 8, wherein the first processor is a graphics processing unit.

* * * * *